United States Patent [19]

Nissen et al.

[11] Patent Number: 5,348,979
[45] Date of Patent: Sep. 20, 1994

[54] METHOD OF PROMOTING NITROGEN RETENTION IN HUMANS

[75] Inventors: Steven L. Nissen, Ames, Iowa; Paul J. Flakoll, Old Hickory, Tenn.; Naji N. Abumrad, Old Field, N.Y.

[73] Assignees: Iowa State University Research Foundation Inc., Ames, Iowa; Vanderbilt University, Nashville, Tenn.

[21] Appl. No.: 996,187

[22] Filed: Dec. 23, 1992

[51] Int. Cl.$^5$ .................. A61K 31/19; A61K 31/335; A23L 1/03
[52] U.S. Cl. .................. 514/557; 514/449; 426/2; 426/531
[58] Field of Search ................ 514/557, 449; 426/2, 426/531

[56] References Cited

U.S. PATENT DOCUMENTS

| | | | |
|---|---|---|---|
| 4,100,161 | 7/1978 | Walser | 424/274 |
| 4,100,293 | 7/1978 | Walser | 424/274 |
| 4,677,121 | 6/1987 | Walser et al. | 514/561 |
| 4,760,090 | 7/1988 | Nissen | 514/561 |
| 4,764,531 | 8/1988 | Nissen | 514/557 |
| 4,992,470 | 2/1991 | Nissen | 514/578 |
| 5,028,440 | 7/1991 | Nissen | 514/557 |
| 5,087,472 | 2/1992 | Nissen | 514/557 |

OTHER PUBLICATIONS

Walser et al., J. Clin. Inv. (1973) 52:678–690.
Saiper and Walser, Metabolism (1977) 26:301–308.
Chawla et al., J. Nutri. (1975) 105:798–803.
Boebel and Baker, J. Nutr. (1982) 112:1929–1939.
Tanaka et al., Biochim. Biophys. Acta. 152:638–641 (1966).
Landass, Clin. Chim. Acta. 64:143–154 (1975).

*Primary Examiner*—Raymond J. Henley, III
*Attorney, Agent, or Firm*—Tilton, Fallon, Lungmus & Chestnut

[57] ABSTRACT

Nitrogen retention in human subjects is promoted by administering β-hydroxy-β-methylbutyric acid (HMB). The amount of HMB administered is effective to conserve protein as determined by reduction in urinary nitrogen. The method can be used with patients having a negative nitrogen balance due to disease conditions, and also with normal elderly persons who are subject to protein loss. The HMB may be administered orally or by intravenous infusion.

14 Claims, No Drawings

METHOD OF PROMOTING NITROGEN RETENTION IN HUMANS

FIELD OF INVENTION

This invention relates to the promotion of nitrogen retention in humans, and more particularly to the administration of therapeutic agents for this purpose.

BACKGROUND OF INVENTION

Tissue proteins forms the basis for organ structure and function. Excessive losses of tissue protein can compromise organ function and eventually will result in death. Any stressful situation such as trauma and chronic debilitating diseases results in tissue losses that if sustained can compromise organ function. In most cases nutrition alone cannot prevent this tissue loss because of excessive breakdown of tissue proteins. Thus alternatives to nutrition must be used to abate or slow the protein wasting or excessive loss of body nitrogen.

Nitrogen balance is the difference between the nitrogen intake (as protein or amino acids) in an individual and the total nitrogen excretion. When the nitrogen intake equals the nitrogen excretion, the subject is in nitrogen equilibrium. If the nitrogen intake exceeds the nitrogen excretion, the nitrogen balance is positive, but if the nitrogen excretion is greater than the nitrogen intake, the nitrogen balance is negative. Nitrogen balance can be estimated by monitoring urinary nitrogen. Absolute nitrogen balance also requires fecal nitrogen measurement, but in most cases this does not change appreciably unless the diet is substantially altered. Thus, the nitrogen content of urine can be approximately correlated with total nitrogen excretion. Monitoring nitrogen content of urine is especially important where the patient has or is expected to have a persistent negative nitrogen balance.

Promoting nitrogen retention has therapeutic importance where the patient has been subjected to trauma or stress conditions which can be expected to induce potential loss. Injury (surgical, traumatic, and burn) and sepsis result in accelerated protein breakdown, which is manifested by increased nitrogen loss. Catabolic conditions are also frequently associated with severe bodily diseases such as cancer, AIDS, etc. Loss of muscle protein may occur due to normal aging, and consequently, protein sparing therapy may be indicated for elderly patients who are otherwise normal.

Therapeutic agents and certain nutritional regimes are known which can promote nitrogen retention. However, therapeutic options to decrease body nitrogen losses (protein wasting) are limited. Injections of certain hormones may improve nitrogen retention. Growth hormone injections can in the short term at least decrease tissue protein losses: Horber et al., *J. Clin. Invest.* (1990) 86: 256. Steroids such as testosterone when injected can decrease nitrogen loss: Daham et al., *Metabolism* (1989) 38: 197. These compounds have to be injected and may have undesirable side effects, limiting usefulness in disease states.

A nutritional approach to protein sparing was investigated by Dr. MacKenzie Walser and associates. They experimented with keto analogs of essential amino acids as partial or complete substitutes for the corresponding amino acids, for example, as supplementation to protein-reduced diets in uremia. [See, for example, Walser et al., *J. Clin. Inv.* (1973) 52: 678–690.] Experiments by Walser and associates demonstrated a nitrogen sparing effect from mixtures of branched-chain keto acids: Saiper and Walser, *Metabolism* (1977) 26: 301–308. Patents have issued to Walser on the use of keto analogs of essential amino acids for promoting synthesis and suppression of urea formation in humans (U.S. Pat. Nos. 4,100,161 and 4,101,293).

The keto acid analog of L-leucine is alpha-ketoisocaproate (KIC) which is also sometime referred to as "keto-leucine". KIC does not have L and D forms as does leucine. It is known that there is an interconversion of circulating KIC and leucine. Published studies have demonstrated that KIC can be substituted in animal diets for leucine providing that larger molar amounts of KIC are used. Chawla et al. reported that weight loss by rats being fed a diet deficient in leucine could be prevented by adding KIC to the diet, but the efficiency of substitution was only 20 to 27%. [*J. Nutr.* (1975) 105: 798–803], and Boebel et al. reported that the efficiency of KIC was only about 56% with reference to leucine [Boebel and Baker, *J. Nutr.* (1982) 112: 1929–1939].

Dr. Steven L. Nissen of Iowa State University, Ames, Iowa, U.S.A. has carried out studies with domestic animals in which KIC is incorporated in the animal feeds. As described in his U.S. Pat. No.4,760,090, it was found that ketoisocaproate (KIC) when fed to cattle and sheep can result in enhancement of growth and feed efficiency. In another use of KIC feeding, egg production of laying chickens was increased (U.S. Pat. No.4,764,531). In later experiments carried by Dr. Nissen at Iowa State University, $\beta$-hydroxy-$\beta$-methylbutyric acid (HMB) was fed to domestic animals. The effects obtained with HMB feeding were different than with KIC.

Metabolically, KIC and HMB are not directly related. KIC is the only metabolic product of leucine, while HMB is a minor product in the metabolic sequence of KIC. Leucine is either used for protein synthesis in the body or is converted directly to KIC. In the mitochondria, KIC is decarboxylated to isovalarylCoA and then further metabolized to ketone bodies. In certain disease conditions, such as isovalaric acidemia, an alternate oxidative pathway for KIC has been observed, which appears to produce $\beta$-hydroxy-$\beta$-methyl-butyrate (HMB). In atypical cases, such as a genetic absence of the dehydrogenase enzyme, there is evidence that HMB can accumulate in the urine: Tanaka, et al. *Biochim. Biosphys. Acta.* 152: 638–641 (1968). Also, in acidosis conditions, HMB levels can be increased in urine: Landass, *Clin. Chim. Acta.* 64: 143–154 (1975).

The differing activities of HMB as fed to domestic animals provided the basis for several patents by Dr. Nissen. U.S. Pat. No. 4,992,470 discloses administration of HMB for enhancing the immune response of mammals, and/or as an ingredient in the raising of meat producing animals (viz. ruminants and poultry) to increase lean tissue development. (See also U.S. Pat. Nos. 5,087,472 and 5,028,440.)

SUMMARY OF INVENTION

This invention is based on the discovery that nitrogen retention in humans can be dramatically improved by the administration of small amounts of $\beta$-hydroxy-$\beta$-methylbutyric acid (HMB). In experiments which lead to the present invention, using normal human subjects nitrogen retention was increased by an average of 18%. This result was unexpected. Heretofore, as far as it is known, there have been no reports of experiments with either humans or animals in which KIC or HMB was administered and effects on nitrogen retention determined. The finding that the administration of one gram of HMB per subject per 24 hours appreciably reduced urinary nitrogen was especially significant since the subjects were well-nourished adults. Prior studies on other means of promoting nitrogen retention have been conducted mostly with subjects under stress conditions who had negative nitrogen balances. A substance that can increase nitrogen retention in humans who are not experiencing a negative nitrogen balance has manifest therapeutic potential.

In accordance with the present invention, HMB can be orally administered to human patients as a protein sparing therapy. At dosages effective for promoting nitrogen retention, HMB is not known to be toxic or to have any undesirable side effects. It can be safely administered to persons afflicted with trauma, stress or other catabolic condition, including people undergoing semi-starvation. HMB can also be used in conjunction with weight reduction programs where it is desired to minimize loss of tissue protein. Moreover, it is believed that HMB can be regularly incorporated in food supplements for the elderly, thereby tend to offset the protein losses which may occur in persons of advanced age. In general, the method of this invention can be used to improve nitrogen balance for human subjects whenever it is medically desirable to counter urinary nitrogen loss which cannot be overcome nutritionally.

DETAILED DESCRIPTION

The base compound for practicing the present invention is β-hydroxy-β-methylbutyric acid (HMB). It can be used in its free acid form or as an edible salt, and edible derivatives of HMB which convert directly in the body to HMB can be used. The free acid compound is also called β-hydroxy-isovalaryic acid. It has the following structure:

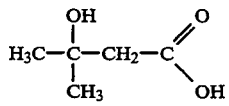

It is preferred to administer HMB as an edible salt, ester, or lactone. The calcium salt is especially convenient because it is less hydroscopic than the sodium or potassium salts. Esters of HMB such as particularly the methyl or ethyl esters are alternative forms. Such esters are rapidly converted in the body to free acid HMB. For administration as a lactone, the compound isovalaryl lactone can be used. This compound and similar lactones are rapidly converted in the body to free acid HMB.

The free acid form can be designated as "HMB-acid", and the salt forms, such as the calcium, sodium, potassium or magnesium salts, respectively, as "Ca-HMB", "Na-HMB", "K-HMB", and "Mg-HMB". Correspondingly, the esters can be designated "HMB-methyl ester", "HMB-ethyl ester", etc. The lactone can be designated "HMB-lactone". HMB has no stero-isomers and accordingly does not exist in L or D forms.

HMB is not commercially available at this time. However, procedures are known for synthesizing this compound from commercially available starting materials. For example, HMB can be synthesized by oxidation of diacetone alcohol (4-hydroxy-4-methyl-2-pentanone). A suitable synthesis procedure is described by Coffman, et al., *J. Am. Chem. Soc.*, 80: 2882-2887, at 2885 (1958). As there described, β-hydroxy-isovalaryic acid (HMB) is prepared by an alkaline sodium hypochlorite oxidation of diacetone alcohol. The product is recovered in free acid form which can be converted to the desired salt. For example, HMB can be prepared as its calcium salt (Ca-HMB) by a similar procedure to that of Coffman, et al. in which the HMB acid obtained is neutralized with calcium hydroxide, and recovered by crystallization from an aqueous ethanol solution. For example, a 95% ethanol solution can be used with the Ca-HMB at about a 10% concentration.

Since Ca-HMB is a preferred form for administering HMB, the dosage amount of HMB can be expressed in terms of corresponding mole amount of Ca-HMB. The dosage range within which HMB can be usefully administered orally or intravenously for promoting nitrogen retention is within the range from 0.01 to 0.2 grams HMB (Ca-HMB basis) per kilogram of body weight per 24 hours. For adults, assuming body weights of from about 100 to 200 lbs., the dosage amount orally or intravenously of HMB (Ca-HMB basis) can range from 0.5 to 10 grams per patient per 24 hours. A presently preferred amount is from 2 to 6 grams HMB (Ca-HMB basis) per patient per 24 hours.

Ca-HMB and other forms of HMB as described above can be processed as fine powders which can be filled into capsules, or combined with tableting diluents, such as lactose, and compressed into tablets of predetermined dose amounts. No special mode of oral administration is needed. One preferred mode is to package the Ca-HMB in water-soluble capsules, such as gelatin capsules. Each capsule may contain as the predetermined amount of the Ca-HMB 0.5, 1, or 2 grams. Multiple doses per day are desirable, and therefore smaller dose sizes are believed preferable. However, if desired, larger doses in capsules or tablets can be prepared, such as 4 grams per capsule or tablet. A suitable regiment for oral administration to adults consists of one tablet or capsule one to four times per 24 hours. Corresponding amounts of HMB can be fed as an ingredient of solid or liquid dietary supplements, such as particularly supplements designed for use by the elderly. Alternatively, Ca-HMB can be dissolved in milk or fruit juice such as orange juice, resulting in a palatable drink.

HMB in a water-soluble non-toxic form can also be administered by intravenous infusion. This method is particularly suitable for hospitalized patients that are on IV therapy. For example, Ca-HMB or Na-HMB can be dissolved in an intravenous solution being administered to the patient, viz. normal saline, glucose, etc. Ca-HMB or Na-HMB may also be added to nutritional IV solutions, which may include amino acids and lipids. The amounts to be administered intravenously can be similar levels to oral administration, but it is believed that a maximized protein retention effect should be obtainable at lower doses by infusion. Infusion also has the advantage that the HMB introduction can be metered and controlled more accurately. For example, beneficial results on nitrogen retention can be obtained by infusion of 0.5 to 10 grams per 24 hours, or preferably from 2 to 6 grams.

The experimental basis of the present invention and the results that can be obtained are further illustrated by the following experimental example.

EXPERIMENTAL EXAMPLE

Preparation of HMB

Ca-HMB was prepared by minor modification of the method of Coffman, et al. *J. Am. Chem. Soc.*, 80: 2882–2887 (1958). More specifically, the crude HMB was first purified by distillation under vacuum, neutralized with Ca(OH)$_2$, and finally the calcium salt crystallization three times from 95% ethanol. The product was then air-dried and fine-ground. Each batch was given a lot number and the purity assessed by high performance liquid chromatography. A single peak was measured when HMB was chromatographed on a C18 column and eluted with 0.01M phosphate buffer, pH 7.0. Also nuclear magnetic resonance was performed. This indicated only two peaks which corresponded to the methyl hydrogens and the CH$_2$ hydrogens. The resulting purified Ca-HMB was used in a human subject study as follows.

Experimental Procedure

In a controlled double-blind human study, the effects of feeding HMB on loss of urinary nitrogen was tested. Effects on blood cholesterol and immune function were also observed. Male subjects (22 to 43 years of age) were used who had been screened for normalcy. They were well-nourished, healthy adults. Ca-HMB was administered in 250 mg capsules. The subjects were instructed to take the capsules in 4 equal doses daily (with meals and at bed time), giving a dose of one gram per subject per 24 hours. The subject ate all their meals under controlled conditions. Normal diets were used, but the amounts of the diets were controlled to maintain equal and substantially constant nitrogen intake. The subjects had blood drawn before the morning meal or before they took the morning HMB dose. Each subject was studied twice: once with a placebo and once with HMB. The subjects did not know which preparations they were given.

The baseline time period consisted of 5 days of controlled dietary treatment followed by a 14 day period of HMB treatment. Urine was quantitatively collected on the last 2 days of the baseline period and the last 4 days of the treatment period.

Urinary nitrogen was quantitated by the Kjeldahl method. The percent nitrogen times the urine volume resulted in grams of urine nitrogen excreted per day. Net change was calculated by subtracting the change during the HMB period from the placebo period. The results are summarized in the accompanying Table A.

TABLE A

|  | Placebo | | HMB | | % Change | | Net % |
| --- | --- | --- | --- | --- | --- | --- | --- |
|  | Baseline | Treatment | Baseline | Treatment | Plac | HMB | HMB Effect |
| Body Weight | 167 | 167 | 176 | 179 | 0 | 1.4 | 1.4 |
| Body fat (%) | 12.4 | 12.0 | 12.5 | 11.0 | −3 | −12 | −9 |
| Urine Nitrogen (g/d) | 14.52 | 16.08 | 16.68 | 15.4 | 10.7 | −7.8 | 18.5 |
| Blood Urea (mg/dl) | 9.20 | 9.68 | 6.80 | 6.58 | 7.2 | −3.4 | −10.7 |

Results

As shown by the data of Table A, HMB decreased the average amount of urine nitrogen by 18% (statistically significant at the $p<0.02$ level). All five subjects decreased urine nitrogen when fed HMB compared to the placebo period. Concomitant with this change was a decrease in blood urea nitrogen. This result suggests that HMB stimulated the retention of dietary protein in body, and presumably this resulted in increased tissue protein retention because dietary nitrogen intake was calculated to be at maintenance. HMB appears to be a potent agent for promoting nitrogen retention even in normal subjects.

We claim:

1. The method of protein sparing, comprising orally or intravenously administering to a human subject an effective amount of $\beta$-hydroxy-$\beta$-methylbutyric acid (HMB) for increasing the retention of nitrogen, said HMB being in an edible or intravenously-administrable form selected from (i) its free acid form, (ii) its sodium, potassium, or calcium salt, (iii) its methyl or ethyl ester, or (iv) its lactone, and continuing the said administration of HMB until the amount of nitrogen in the patient's urine has substantially decreased.

2. The method of claim 1 in which said HMB is in the form of its calcium salt (Ca-HMB) or its sodium salt (Na-HMB).

3. The method of claims 1 or 2 in which said effective amount of HMB is within the range from 0.01 to 0.20 grams of said HMB based on its calcium salt per kilogram body weight per 24 hours.

4. The method of claims 1 or 2 in which said HMB is administered orally.

5. The method of claims 1 or 2 in which said HMB is administered by intravenous infusion.

6. The method of treating an adult human patient having a negative nitrogen balance, comprising orally or intravenously administering to the patient from 0.5 to 10 grams per 24 hours of $\beta$-hydroxy-$\beta$-methylbutyric acid (HMB) based on its calcium salt, said HMB being in an edible or intravenously-administrable form selected from (i) its free acid form, (ii) its sodium, potassium, magnesium, or calcium salt, (iii) its methyl or ethyl ester, or (iv) its lactone, and continuing the said administration of HMB until the loss of nitrogen is substantially reduced as determined by nitrogen analysis of the patient's urine.

7. The method of claim 6 in which said HMB is in the form of its calcium salt (Ca-HMB).

8. The method of claim 6 in which said HMB is in the form of its sodium salt (Na-HMB).

9. The method of claims 6, 7 or 8 in which said HMB is administered orally to the human patient in an amount of from 2 to 6 grams per 24 hours based on its calcium salt.

10. The method of claims 6, 7 or 8 in which said HMB is administered by intravenous infusion in an amount of 2 to 6 grams per 24 hours.

11. The method of improving protein nutrition in elderly human subjects, comprising including in the daily diets of the human subjects an amount of from 0.5 to 10 grams per 24 hours of $\beta$-hydroxy-$\beta$-methylbutyric acid (HMB) based on its calcium salt, said HMB being in an edible form selected from (i) its free acid form, (ii) its sodium, potassium, or calcium salt, (iii) its methyl or ethyl ester, or (iv) its lactone, said amount of said HMB incorporated in said diets being effective to reduce the urinary nitrogen losses of the subjects.

12. The method of claim 11 in which said HMB is in the form of its calcium salt (Ca-HMB).

13. The method of claims 11 or 12 in which the amount of HMB incorporated in said daily diets is from 2 to 6 grams per 24 hours.

14. The method of treating a human patient who is receiving an intravenous therapy and is subject to excessive loss of nitrogen, comprising incorporating in an intravenous solution being given to the human patient an effective amount of HMB for reducing urinary nitrogen, said HMB being in an intravenously administerable form selected from Ca-HMB or Na-HMB.

* * * * *